Feb. 5, 1974 R. L. BYRUM Plant Pat. 3,466
ROSE PLANT
Filed May 24, 1972
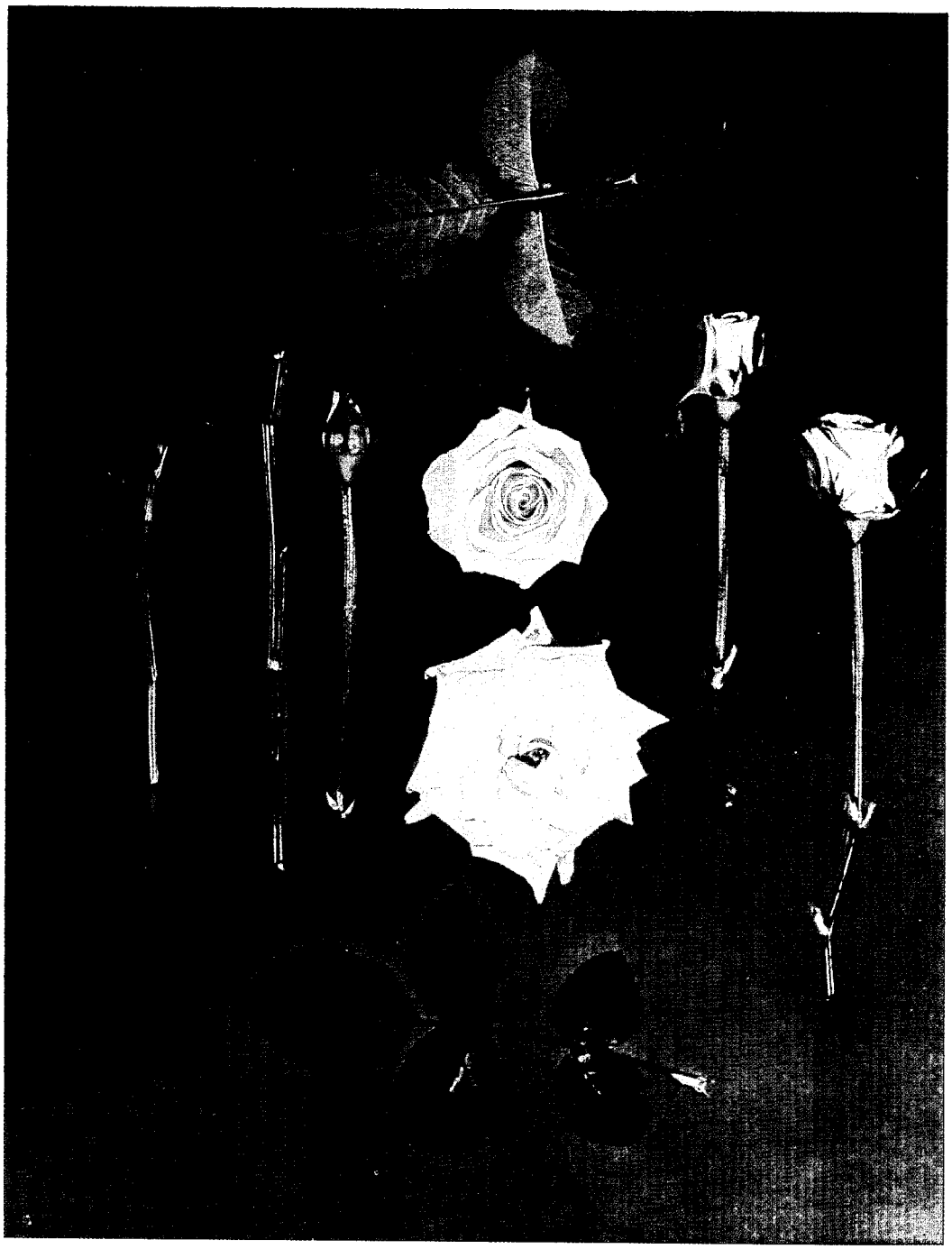

United States Patent Office

Plant Pat. 3,466
Patented Feb. 5, 1974

3,466

ROSE PLANT

Roy L. Byrum, Richmond, Ind., assignor to Joseph H. Hill Company, Richmond, Ind.

Filed May 24, 1972, Ser. No. 256,620
Int. Cl. A01h 5/00
U.S. Cl. Plt.—26 1 Claim

ABSTRACT OF THE DISCLOSURE

A new variety of pink floribunda rose for greenhouse culture distinguished by its free propagating ability, its vigorous growth habit, and its continuous and abundant production of medium sized blooms having a very attractive Dawn Pink to French Rose coloring.

BACKGROUND OF THE INVENTION

My new variety of rose plant was developed as a seedling resulting from a crossing of Seventeen (P.P. 1,765) with Gemini (P.P. 2,728) which I made in the Spring of 1966 at Richmond, Ind., during the course of a breeding program carried on with the object of developing an improved variety of pink flowering plant which would be better producer, which would propagate freely and be disease resistant, and which would provide an attractive flower having a longer vase life in the home.

This seedling was selected for propagation and test in the Fall of 1967 when it became apparent that both the plant and its blooms had the desirable characteristics which were sought and asexual propagation of the plant by budding, carried on at Hamilton City, Calif., has demonstrated that the desirable and distinctive characteristics of this new variety are fixed and hold true through successive propagations.

Successive generations of this new variety of pink rose have been grown under glass at Richmond, Ind., since 1969 and the following observations were made at Richmond, Ind., in November 1971.

DESCRIPTION OF THE DRAWING

This new variety of rose plant is illustrated by the accompanying full color drawing which shows the form of the newly opened flower positioned above the face view of a blossom newly opened. This illustration also shows very young wood with leaves, mature wood, buds in three stages of opening, and the upper and under side of typical leaves.

DESCRIPTION OF THE PLANT

The following is a detailed description of my new variety of rose plant with color designations according to Koster's Color Guide (K) and Robert S. Wilson's Horticultural Colour Chart (W).

*The plant*

Origin: Seedling (67–55P)
Parentage:
- Seed parent—Seventeen (P.P. 1,765)
- Pollen parent—Gemini (P.P. 2,728)

Classification: Floribunda
Form: Bush
Habit: Upright and much branched
Growth: Free and vigorous with canes of medium diameter
Main stems: Color—Sage Green 000861/2 (W) overlaid with streaks of Tobacco Brown, Plate No. 88 (K)
- *Thorns.*—Very few, of short length and hooked downward with short, narrow base. Color—Tobacco Brown, Plate No. 88 (K)
- *Prickles and hairs.*—None Branches: Color—Spinach Green 0960 (W)
- *Thorns.*—Very few, of short length and hooked downward from a short narrow base. Color—Rose Opal 022/2 (W)
- *Prickles.*—Several with color of Rose Opal 022/3 (W)
- *Hairs.*—None New shoots: Color—Pod Green 061/3 (W) shaded with Oxblood Red 00823/3 (W)
- *Thorns.*—Very few, of short length and hooked downward. Color—Oxblood Red 00823/3 (W)
- *Prickles and hairs.*—None Foliage: Quantity—Abundant
- *Leaves.*—Size—Medium. Shape—odd pinnate. Aspect—Moderately heavy
- *Leaflets.*—5 to 7 in number, occasionally 3. Shape—Elliptical, with round base, acute apex and simply serrate margin. Color—Young: Upper side Oxblood Red 00823 (W); under side, Oxblood Red 00823/3 (W); mature: Upper side, Spinach Green 0960/2 (W) with Dark Violet, Plate No. 58 (K), edges and veins; under side, Sage Green, Plate No. 78 (K)
- *Rachis.*—Medium heavy, with grooved upper side and moderately prickly under side
- *Stipules.*—Medium length and width with short points turning outward at an angle of less than 45°

*The bud*

Before calyx breaks:
- *Size.*—Medium small
- *Form.*—Short pointed, with a conspicuous neck and having foliaceous appendages on the surface of the bud which have much cut parts extending beyond the tip of the bud a distance of one quarter or more of the bud length
- *Color of calyx.*—Scheeles Green 860/2 (W)

As calyx breaks: Color of bud—Vermilion 18/3 (W)
As first petal opens:
- *Size.*—Medium small
- *Form.*—Short pointed
- *Color.*—Outside of petals—Shrimp Red 616/3 (W). Inside of petals—Shrimp Red 616/2 (W)

Bud opening: Bud opens very well in greenhouse
Sepals: Permanent, spear shaped, curled and of medium length
- *Color.*—Inside—Scheeles Green 860/3 (W) overlaid with white fuzz. Outside—Scheeles Green 860/2 (W) with a margin of Veronese Green 660/1 (W)
- *Peduncle.*—Erect, long and of medium diameter
- *Bark.*—Almost smooth. Color of bark—Scheeles Green 860/2 (W)
- *Thorns.*—None
- *Prickles.*—Few
- *Hairs.*—None
- *Color.*—Orient Pink 416/3 (W)

*The flower*

Blooming habit: Abundant and continuous
Size: Medium—1½ to 2½ inches
Borne: Singly, on medium strong stems of medium length
Form: Full at first, with petals tightly rolled outward, becoming open at maturity with petals remaining outwardly rolled
Petalage: Very double with 30 to 35 petals arranged regularly
- *Shape of petals.*—Obovate with mucronate apex—some inside petals are spatulate with one notch

Color

Of a newly opened flower in greenhouse:

Outside petals:
- *Outside surface.*—Rose Pink 427/3 (W) with shades of Primrose Yellow 601/2 (W) to 601/3 (W) at base of petal

*Inside surface.*—Rose Pink 427/2 (W) at top of petal changing through Rose Pink 427/3 (W) to Mimosa Yellow 602/2 (W) at base of petal Intermediate petals:

*Outside surface.*—Pale Reddish Lilac, Plate No. 35 (K) in body of petal changing to Rose Pink 427/2 (W) at top of petal

*Inside surface.*—Rose Pink 427/2 (W) at top changing through Rose Pink 427/3 (W) to Mimosa Yellow 602/2 (W) at base Inner petals:

*Outside surface.*—Pale Lilac Rose, Plate No. 34 (K), gradually changing to Mimosa Yellow 602/2 (W) at base

*Inside surface.*—Pale Lilac Rose, Plate No. 34 (K), changing to Mimosa Yellow 602/2 (W) at base of petal Of a flower opened for three days:

Outside petals:

*Outer surface.*—Rose Pink 427/3 (W) with a base of Primrose Yellow 601/3 (W)

*Inside surface.*—Rose Pink 427/2 (W) with Primrose Yellow 601/2 (W) at base of petal Intermediate petals:

*Outside surface.*—Rose Pink 427/3 (W) with Primrose Yellow 601/3 (W) at base of petal

*Inside surface.*—Rose Pink 427/2 with base of petal Primrose Yellow 601/2 (W)

Inner petals:

*Outside surface.*—Rose Pink 427/3 (W) with Primrose Yellow 601/2 (W) at base of petal

*Inside surface.*—Rose Pink 427/2 (W) with base of petal Primrose Yellow 601/2 (W)

General color effect of the open bloom:

*Newly opened flower.*—Dawn Pink 523/2 (W)

Three days opened flower.—French Rose 520/3 (W)

Texture of petals: Moderately thick, firm and leathery

Appearance of petals:

*Inside*—Shiny and satiny

*Outside.*—Shiny

Presistence: Petals hang on and dry

Fragrance: Moderate tea

Lasting quality: 4 to 5 days at living room temperatures in November 1971

*Reproductive organs*

Stamens: Many—regularly arranged about the pistils

*Filaments.*—Short—most with anthers. Color—Barium Yellow 503/2 (W)

*Anthers.*—Small—all open at once. Color—Maize Yellow 607/2 (W)

*Pollen.*—Moderate in amount. Color—Amber Yellow 505/2 (W)

Pistils: Medium in number

*Styles.*—Short, thin, of even length and bunched. Color—Pure White, Plate No. 1 (K)

*Stigmas.*—Color—Creamy White, Plate No. 2 (K)

Ovularies: Some protruding from calyx

Seeds: None

My new variety of rose plant is quite dissimilar with respect to other pink roses becauses of its size, color and vigorous growth habits. It is distinguished from its seed parent, Seventeen (P.P 1,765), in that it has more vigorous growth and propagates freely whereas the seed parent was difficult to propagate with any degree of consistency. My new variety is distinguished from its pollen parent, Gemini (P.P. 2,728), by its entirely different color which gives it a greatly enhanced acceptability and range of usage.

My new variety of rose is an upright, vigorous grower and is virtually disease resistant, as observed at Richmond, Ind., and Hamilton City, Calif. The reflexed petals of the opened flower gives it a star-shaped effect which is very distinctive and the abundance of lush, dark green foliage accentuates and enhances the color of the flower.

I claim:

1. A new and distinct variety of rose plant substantially as herein shown and described, characterized by the novel pink color of its flowers, its vigorous growth habit and abundant production of flowers, and its ability to be freely propagated.

No references cited.

ROBERT E. BAGWILL, Primary Examiner